United States Patent [19]

Kayane et al.

[11] Patent Number: 4,787,940

[45] Date of Patent: Nov. 29, 1988

[54] METHOD FOR PURIFYING SUGAR PHOSPHATES OR THEIR SALTS

[75] Inventors: Shigeto Kayane; Mitsugu Morishita; Takashi Imamura; Masanobu Tanigaki, all of Wakayama; Tomihiro Kurosaki, Osaka, all of Japan

[73] Assignee: Kao Corporation, Tokyo, Japan

[21] Appl. No.: 12,496

[22] Filed: Feb. 9, 1987

[30] Foreign Application Priority Data

Feb. 20, 1986 [JP] Japan .................................. 61-36441

[51] Int. Cl.$^4$ .......................... C13D 3/18; B01D 17/06
[52] U.S. Cl. .................................... 127/54; 536/127;
204/182.3; 204/182.4; 204/182.6; 204/186;
204/138; 127/10
[58] Field of Search ............... 127/54, 10; 536/127;
204/182.3, 182.6, 186, 138, 182.4

[56] References Cited

U.S. PATENT DOCUMENTS

| 751,179 | 2/1904 | Kollrepp et al. ............ 127/54 |
| 4,492,601 | 1/1985 | Nakasone et al. ............ 127/54 |
| 4,650,862 | 3/1987 | Imamura et al. ............ 536/117 |

FOREIGN PATENT DOCUMENTS

| 40-15172 | 7/1965 | Japan . |
| 58-32597 | 7/1983 | Japan . |
| 30700 | 2/1985 | Japan .................................. 127/46.2 |

OTHER PUBLICATIONS

*Arch. Biochem.*, 4, 11 (1944) J. B. Summer et al "Prep. of Glucose -1-Phosphate.

*J. Am. Chem. Soc.*, 66, 560 (1944) R. M. McCready et al. "Prep. and Purif. of Glucose-1-Phosphate by the Aid of Ion Exchange Absorbents."

*Primary Examiner*—H. M. S. Sneed
*Assistant Examiner*—Chung K. Pak
*Attorney, Agent, or Firm*—Oblon, Fisher, Spivak, McClelland & Maier

[57] ABSTRACT

A novel method for purifying a sugar phosphate or its salt, in which a sugar-containing mixture of a sugar phosphate or its salt and phosphoric acid or its salt is subjected to electrodialysis to remove the phosphoric acid or its salt from the mixture.

According to this method, the phosphoric acid or its salt can be readily obtained in a reusable form. The method is thus quite advantageous in view of the economy.

6 Claims, No Drawings

METHOD FOR PURIFYING SUGAR PHOSPHATES OR THEIR SALTS

BACKGROUND OF THE INVENTION

1. Field of the Invention

This invention relates to a method for purifying or refining sugar phosphates or their salts and more particularly to a method for purifying sugar phosphates or their salts by electrodialysis.

The term "electrodialysis" used herein is intended to mean a technique in which there is provided a multiple chamber-type dialyzing vessel which has cation exchanger membranes capable of passing cations and anion exchanger membranes capable of passing anions arranged alternately and is provided with electrodes at opposite ends of the vessel, and a direct current is passed across the electrodes to move anions toward the anode and cations toward the cathode.

2. Description of the Prior Art

Sugar phosphates are compounds present abundantly in living bodies and are known as being useful. For instance, glucose-1-phosphate is useful as an antibacterial agent for medicines, an antitumor agent (platinum complex) and a curing agent for heart diseases (amine salts). Glucose-6-phosphate is useful as an acute hemorrhage curing agent for low blood pressure patients or reagent for analyzing substances in living body such as, for example, a glucose-6-phosphate dehydrogenase, a glucose-6-phosphate esterase and the like.

Heretofore, various processes of preparing sugar phosphates are known, including, for example, a process in which a glucan and an orthophosphate are reacted in the presence of a phosphorylase to obtain glucose-1-phosphate [J. B. Summer et al, Arch. Biochem., 4, 11 (1944) and R. M. McCready et al, J. Am. Chem. Soc., 66, 560(1944)], a process of preparing glucose-6-phosphate by reaction between glucose and metaphosphoric acid or a polyphosphoric acid in the presence of a microorganism such as belonging to the Acromobacter (Japanese Patent Publication No. 58-32597), and a process of preparing glucose-6-phosphate by reaction between glucose and a polyphosphoric acid (Japanese Patent Publication No. 40-15172).

When, however, orthophosphates or polyphosphoric acid is used as a phosphorylating agent as in these processes, it is inevitable that orthophosphates or polyphosphoric acid be contained in the resultant sugar phosphates.

However, when large amounts of orthophosphates or polyphosphoric acid is contained in the sugar phosphates or their salts, unfavorable influences may be produced depending on the use, for instance, in case where the sugar phosphates or their salts are used as a medicine or a reagent for analysis of substances in the living body.

In general methods of separating a large amount of phosphoric acid or its salt from a mixture of sugar phosphates or their salts and phosphoric acid or its salt, phosphoric acid or its salt is insolubilized by conversion into $Ba_3(PO_4)_2$, $Mg_3(PO_4)_2$, $Li_3PO_4$, $MgNH_4PO_4$ and the like. These methods undesirably require the step of filtering the insolubilized phosphoric acid salts, thus making the process complicated and/or involving a loss of the sugar phosphates in the filter cake. Thus, these methods are not favorable as an industrial separation and purification method. In addition, a large amount of the phosphoric acid salts is wasted with a very poor economy.

Accordingly, there is a demand of the development of a purification method for the separation of sugar phosphates or their salts from phosphoric acid or its salt in which the phosphoric acid or its salt can be separated readily and in a re-utilizable form.

SUMMARY OF THE INVENTION

The present inventors made intensive studies to solve the above problems. As a result, it was found that despite the fact that desalting of anionic active agents, such as sodium salts of alkylsulfates, by electrodialysis is known to be difficult for the reason that the sodium salt of alkylsulfates deposit on the cationic exchange membrane, sugar phosphates or salts thereof do not deposit on a cationic exchange membrane, if desalted by electrodialysis in the presence of a certain amount of sugar. Accordingly, the sugar phosphates or salts thereof can be separated from phosphoric acid or its salts efficiently, readily and in a re-utilizable form by proper selection of a size of an ion exchange membrane. The present invention is accomplished based on the above finding.

The present invention provides a method for purifying sugar phosphates or their salts which is characterized by separating phosphoric acid or its salt from a mixture of sugar phosphates or their salts and phosphoric acid or its salts, which contains a certain amount of sugar, by electrodialysis.

DETAILED DESCRIPTION OF THE INVENTION AND PREFERRED EMBODIMENTS

The sugar phosphates or their salts used in the practice of the invention include, for example, phosphates of monosaccharides such as hexose, pentose and the like, and polysaccharides such as disaccharides and the like, and their salts of alkali metals such as sodium, potassium and the like. More particularly, there can be mentioned glucose-1-phosphate, glucose-6-phosphate, mannose-6-phosphate, galactose-6-phosphate, fructose-6-phosphate, glucose-1,6-diphosphate, fructose-1,6-diphosphate, their salts with alkali metals such as sodium, potassium and the like. A sugar which must be present when the mixture is subjected to electrodialysis may be either mono-saccharides such as hexose and pentose, disaccharides or polysaccharides. Specific examples are glucose, maltose, maltotriose, maltotetraose, maltopentaose, mannose, galactose, fructose, etc.

Phosphoric acid or its salts to be separated may be, for example, orthophosphoric acid, polyphosphoric acids such as pyrophosphoric acid, and salts with alkali metals such as sodium, potassium and the like.

The method of the invention comprises subjecting an aqueous solution of a mixture of sugar phosphates or salts thereof, phosphoric acid or its salt, and a sugar (hereinafter referred to as stock solution) to electrodialysis and collecting the dialyzed stock solution.

The electrodialysis is effected by placing the stock solution in a partitioned chamber of a multichamber dialyzing vessel and water or an aqueous solution having a low concentration of a salt (hereinafter referred to as an electrolytic solution) in adjacent chambers. The most preferable salt for the electrolytic solution is a phosphoric acid salt. The content of a sugar in the aqueous solution should be not less than 0.5 g/l, and is preferably 1 g/l. There is no specific upper limit on the sugar content of the solution although 300 g/l may be preferable in view of the economy and operability of the electrodialyzing process. Other operating conditions, i.e., the concentration of the stock solution, a concentration of the electrolytic solution, an electrodialysis time, a quantity of electric current, an area of the membrane and the like, may be determined depending on the purpose. The quantity of electric current, however, is preferably determined within a range not exceeding a threshold current density.

A large amount of phosphoric acid or its salts separated in the electrolytic solution can be collected and re-used in the form of phosphoric acid or its salt by concentrating the electrolytic solution or topping of water. Although phosphoric acid or its salt is left in the stock solution in small amounts, this may be removed, after concentration of the stock solution, by subjecting the solution again to electrodialysis or by insolubiling the phosphate. The sugar contained in the refined sugar phosphate solution may be eliminated by means of the ion-exchange, the recrystallization, and the like method.

subjected to electrodialysis contained 2.9 g/l of sugars, of which 2.3 g/l was glucose and 0.2 g/l was maltose.

For the electrodialysis, anion and cation exchange membranes using styrenedivinylbenzene produced by Tokuyama Soda Co., as a base material, were alternately assembled to form a multi-chamber electrodialyzing apparatus. The total area of the membranes used was 0.21 m$^2$ for the anion exchange membrane and the cation exchange membrane, respectively.

2000 ml of the aqueous solution of the above composition was circulated to each of every other partitioned chambers of the dialyzing vessel, while 2000 ml of a 1.0% potassium phosphate aqueous solution (pH 7.0) was passed through each of the adjacent chambers, both at a linear velocity of not lower than 1.5 cm/second so that a pressure at opposite sides of the membrane became constant. An electric current was passed at an average current density of 0.34 A/cm$^2$ for 9 hours. The result is shown in the table below. The recovery of the potassium glucose-1-phosphate was 80.6% and the removal rate of the potassium phosphate was 99.0%.

|  | Prior to Dialysis | | | After Dialysis | | |
| --- | --- | --- | --- | --- | --- | --- |
|  | Concentration (mmol/l) | Amount of Solution (ml) | Content (mmol) | Concentration (mmol/l) | Amount of Solution (ml) | Content (mmol) |
| Potassium glucose-1-phosphate | 38.9 | 2000 | 77.8 | 41.8 | 1560 | 62.7 |
| Potassium phosphate | 505.1 | 2000 | 1010.2 | 7.5 | 1560 | 11.7 |

The purification method for sugar phosphates or their salts of the invention makes use of electrodialysis, so that phosphoric acid or its salts usually contained in large amounts in the sugar phosphates or their salts can be readily and very efficiently separated and removed. In addition, the phosphoric acid or its salts may be obtained in a reusable form, thus making the method very advantageous in view of the economy.

The present invention is described by way of examples.

EXAMPLE 1

27 g of potato starch was mixed with a small amount of water to obtain a starch milk, which was poured into 1000 ml of boiling water while agitating, thereby obtaining a starch paste. After cooling, the paste was added with 600 ml of an aqueous solution containing 116 g of K$_2$HPO$_4$ and 79.4 g of KH$_2$PO$_4$, 800 ml of a potato juice, which was obtained by mashing 2 kg of potato and subjecting the mashed potato to a centrifugal separation, and 5 cc of toluene, thus making the total volume of the mixture to 2500 ml, which was allowed to react at 40° C. for 24 hours. The resulting mixture of the potassium salt of glucose-1-phosphate and potassium phosphate was subjected to electrodialysis to remove the potassium phosphate. The mixture before being

EXAMPLE 2

27 g of potato starch was mixed with a small amount of water to obtain a starch milk, which was poured into 1000 ml of boiling water while agitating. After cooling, the paste was added with 600 ml of an aqueous solution containing 116 g of K$_2$HPO$_4$ and 79.4 g of KH$_2$PO$_4$, 800 ml of a potato juice, which was obtained by mashing 2 kg of potato and subjecting the mashed potato to a centrifugal separation, and 5 cc of toluene, thus making the total volume of the mixture to 2500 ml, which was allowed to react at 40° C. for 24 hours. The resulting mixture of the sodium salt of glucose-1-phosphate and sodium phosphate, containing 2.8 g/l of sugars same as in Example 1, was subjected to electrodialysis in the same manner as in Example 1 to remove the potassium phosphate. As a result, 74.8% of the sodium glucose-1-phosphate was recovered and 99.4% of the sodium phosphate was removed.

|  | Prior to Dialysis | | | After Dialysis | | |
| --- | --- | --- | --- | --- | --- | --- |
|  | Concentration (mmol/l) | Amount of Solution (ml) | Content (mmol) | Concentration (mmol/l) | Amount of Solution (ml) | Content (mmol) |
| Sodium glucose-1-phosphate | 39.3 | 2000 | 78.6 | 36.8 | 1600 | 58.8 |
| Sodium phosphate | 504.7 | 2000 | 1009.4 | 3.9 | 1600 | 6.2 |

EXAMPLE 3

An aqueous solution containing glucose-6-phosphate, orthophosphoric acid was 4.2 g/l of glucose, prepared according to a known method (Japanese Patent Publication No. 40-15172), was neutralized with KOH for conversion into potassium glucose-6-phosphate and potassium phosphate, and then subjected to electrodialysis under the same conditions as in Example 1 to effect desalting of the potassium phosphate. As a result, potassium glucose-6-phosphate was obtained at a recovery of 75.0% and 99.5% of potassium phosphate was removed.

|  | Prior to Dialysis | | | After Dialysis | | |
|---|---|---|---|---|---|---|
|  | Concentration (mmol/l) | Amount of Solution (ml) | Content (mmol) | Concentration (mmol/l) | Amount of Solution (ml) | Content (mmol) |
| Potassium glucose-6-phosphate | 36.4 | 2000 | 72.6 | 43.6 | 1250 | 54.5 |
| Potassium phosphate | 878.0 | 2000 | 1756.0 | 7.2 | 1250 | 9.0 |

EXAMPLE 4

An aqueous solution containing glucose-6-phosphate, orthophosphoric acid and 4.2 g/l of glucose, prepared according to a known method (Japanese Patent Publication No. 40-15172), was neutralized with NaOH for conversion into sodium glucose-6-phosphate and sodium phosphate, and then subjected to electrodialysis under the same conditions as in Example 1 to effect desalting of the sodium phosphate. As a result, sodium glucose-6-phosphate was obtained at a recovery of 78.5% and 99.2% of sodium phosphate was removed.

|  | Prior to Dialysis | | | After Dialysis | | |
|---|---|---|---|---|---|---|
|  | Concentration (mmol/l) | Amount of Solution (ml) | Content (mmol) | Concentration (mmol/l) | Amount of Solution (ml) | Content (mmol) |
| Sodium glucose-6-phosphate | 35.9 | 2000 | 71.8 | 44.0 | 1280 | 56.4 |
| Sodium phosphate | 885.4 | 2000 | 1770.8 | 11.1 | 1280 | 14.2 |

EXAMPLE 5

27 g of potato starch was mixed with a small amount of water to obtain a starch milk, which was poured into 1000 ml of boiling water while agitating, thereby obtaining a starch paste. After cooling, the paste was added with 600 ml of an aqueous solution, which was obtained by concentrating 2300 ml of the electrolytic solution of Example 1 (997 mmols of potassium phosphate and 15.1 mmols of potassium glucose-1-phosphate) by distillation under reduced pressure and adjusted pH 7.0 by 1N KOH, 800 ml of a potato juice obtained by mashing 2 kg of potato with a juicer and subjecting the resulting juice to centrifugal separation, and 5 cc of toluene, thus making the mixture to a total volume of 2500 ml. This mixture was allowed to react at 40° C. for 24 hours. The resulting mixture of the potassium salt of glucose-1-phosphate and potassium phosphate, containing 3.5 g/l of sugars same as in Example 1, was subjected to electrodialysis in the same manner as in Example 1 to remove the potassium phosphate. As a result, 80.9% of sodium glucose-1-phosphate was recovered and 98.8% of potassium phosphate was removed.

|  | Prior to Dialysis | | | After Dialysis | | |
|---|---|---|---|---|---|---|
|  | Concentration (mmol/l) | Amount of Solution (ml) | Content (mmol) | Concentration (mmol/l) | Amount of Solution (ml) | Content (mmol) |
| Potassium glucose-1-phosphate | 44.5 | 2000 | 88.9 | 44.4 | 1620 | 71.98 |
| Potassium phosphate | 460.1 | 2000 | 920.2 | 6.8 | 1620 | 11.0 |

EXAMPLE 6

A solution (pH 7.0) with a composition shown in the table below was prepared using purified potassium glucose-1-phosphate, potassium phosphate and glucose. This solution was subjected to electrodialysis in the same conditions as in Example 1 to remove potassium phosphate therefrom. As a result, 82.0% of potassium glucose-1-phosphate was recovered and 99.2% of potassium phosphate was removed.

|  | Prior to Dialysis | | | After Dialysis | | |
|---|---|---|---|---|---|---|
|  | Concentration (mmol/l) | Amount of Solution (ml) | Content (mmol) | Concentration (mmol/l) | Amount of Solution (ml) | Content (mmol) |
| Potassium glucose-1-phosphate | 40.1 | 2000 | 80.2 | 41.6 | 1580 | 65.8 |
| Potassium phosphate | 502.0 | 2000 | 1004.0 | 5.1 | 1580 | 8.0 |
| Glucose | 1 (g/l) | 2000 | 2 | — | — | — |

EXAMPLE 7

A solution (pH 7.0) with a composition shown in the table below was prepared using purified potassium glucose-1-phosphate, potassium phosphate and dextrin in an amount of 11.26 DE (dextrose equivalent). This solution was subjected to electrodialysis in the same conditions as in Example 1 to remove potassium phosphate therefrom. As a result, 81.0% of potassium glucose-1-phosphate was recovered and 98.7% of potassium phosphate was removed.

| | Prior to Dialysis | | | After Dialysis | | |
|---|---|---|---|---|---|---|
| | Concentration (mmol/l) | Amount of Solution (ml) | Content (mmol) | Concentration (mmol/l) | Amount of Solution (ml) | Content (mmol) |
| Potassium glucose-1-phosphate | 35.8 | 2000 | 71.6 | 31.7 | 1830 | 58.0 |
| Potassium phosphate | 484.5 | 2000 | 969.0 | 7.1 | 1830 | 13.0 |
| Dextrin | 3.2 (g/l) | 2000 | 6.4 (g) | — | — | — |

COMPARATIVE EXAMPLE 1

A solution (pH 7.0) with a composition shown in the table below was prepared using purified potassium glucose-1-phosphate, potassium phosphate and glucose. This solution was subjected to electrodialysis in the same conditions as in Example 1 to remove potassium phosphate. As a result, 100% of potassium phosphate was removed, but the recovery rate of potassium glucose-1-phosphate was only 33.4%.

| | Prior to Dialysis | | | After Dialysis | | |
|---|---|---|---|---|---|---|
| | Concentration (mmol/l) | Amount of Solution (ml) | Content (mmol) | Concentration (mmol/l) | Amount of Solution (ml) | Content (mmol) |
| Potassium glucose-1-phosphate | 37.9 | 2000 | 75.8 | 17.6 | 1440 | 25.3 |
| Potassium phosphate | 489.0 | 2000 | 978.0 | 0 | 1440 | 0 |

COMPARATIVE EXAMPLE 2

An electrodialysis method and a method of converting a phosphate into an insolubilized salt ($MgNH_4PO_4$) were, respectively, used to remove potassium phosphate from a reaction solution prepared in the following manner to compare the recovery rate of potassium glucose-1-phosphate by these two methods.

(Reaction Solution)

27 g of potato starch was mixed with a small amount of water to obtain a starch milk, which was poured into 1000 ml of boiling water while agitating for conversion into a paste. After cooling, there were added, to the paste, 600 ml of an aqueous solution containing 116 g of $K_2HPO_4$ and 79.4 g of $KH_2PO_4$, 800 ml of a potato juice obtained by mashing 2 kg of potato in a juicer and subjecting to centrifugal separation and 5 cc of toluene, thus bringing the solution to a total volume of 2500 ml. The thus obtained mixture was allowed to react at 40° C. for 24 hours, thereby obtaining a solution of potassium glucose-1-phosphate, comprising 2.9 g/l of sugars containing glucose as a major component.

(Recovery)

| Removal Method | Recovery (%) |
|---|---|
| Electrodialysis | 92.3 |
| Insolubilization Method | 75.2 |

The recovery of the electrodialysis method is determined by repeating the following procedure five times.

The reaction solution was subjected to electrodialysis to remove an aqueous solution of the potassium phosphate. The removed potassium phosphate aqueous solution was concentrated by distillation under reduced pressure, after which the pH was adjusted to 7.0 by the use of 1N KOH and a total volume of the solution was made to 600 ml. This solution was added, along with 800 ml of a potato juice and 5 cc of toluene, to a previously prepared starch solution (i.e. an aqueous solution obtained by making a starch milk from 27 g of potato starch and a small amount of water, pouring the milk into 1000 ml of boiling water while agitating to make a paste and cooling the paste), to bring the solution to a volume of 2500 ml in total. The solution was allowed to react at 40° C. for 24 hours. The resulting reaction solution was again subjected to electrodialysis to remove potassium phosphate, thereby collecting potassium glucose-1-phosphate.

From the above results, it was found that the intended product was obtained at a high yield by the use of the recovered phosphate and that when the recovered phosphate was repeatedly used, the intended product was recovered at a very high yield.

What is claimed is:

1. A method for purifying a feed material selected from the group consisting of glucose-1-phosphate, glucose-6-phosphate, fructose-6-phosphate, glucose-1,6-diphosphate, fructose-1,6-diphosphate and a sodium or potassium salt thereof and mixtures thereof; said feed material further containing as an impurity phosphoric acid, an alkali metal salt of phosphoric acid, or a mixture thereof, which comprises electrodialyzing said mixture in the presence of a mono- or polysaccharide in an amount of at least 0.5 g/l.

2. The method according to claim 1, wherein said phosphoric acid is orthophosphoric acid or a polyphosphoric acid and said alkali metal salt of phosphoric acid is a sodium or potassium salt of phosphoric acid.

3. The method according to claim 1, wherein said monosaccharide is selected from the group consisting of glucose, mannose, galactose and fructose; and said polysaccharide is selected from the group consisting of maltotriose, maltotetrose maltopentose, and maltose.

4. The method according to claim 1, wherein for said electrodialysis, said feed material is placed in a partition chamber of a multi-chamber dialyzing vessel, and water or an electrolytic salt solution placed in adjacent chambers.

5. The method according to claim 1, wherein for said electrodialysis, a quantity of electrocurrent is used not exceeding a threshold current density.

6. The method according to claim 1, wherein said electrodialysis is effected using cation and anion exchange membranes made of styrenedivinylbenzene as a base material.

* * * * *